(12) United States Patent
Matyas et al.

(10) Patent No.: US 11,116,641 B2
(45) Date of Patent: Sep. 14, 2021

(54) ORTHOPAEDIC PROSTHETIC SYSTEM FOR A ROTATING HINGED-KNEE PROSTHESIS

(71) Applicant: DePuy Ireland Unlimited Company, Ringaskiddy (IE)

(72) Inventors: Aaron J. Matyas, Fort Wayne, IN (US); Tyler S. Hathaway, Auburn, IN (US); Paul B. Sade, Sr., Churubusco, IN (US); Nathan C. Reeder, Warsaw, IN (US); Kyle D. Steffe, Warsaw, IN (US); David E. Rottger, Auburn, IN (US); Anthony J. Webb, Fort Wayne, IN (US)

(73) Assignee: DEPUY IRELAND UNLIMITED COMPANY

( * ) Notice: Subject to any disclaimer, the term of this patent is extended or adjusted under 35 U.S.C. 154(b) by 400 days.

(21) Appl. No.: 16/267,687

(22) Filed: Feb. 5, 2019

(65) Prior Publication Data
US 2020/0246150 A1 Aug. 6, 2020

(51) Int. Cl.
*A61F 2/38* (2006.01)

(52) U.S. Cl.
CPC .............. *A61F 2/389* (2013.01); *A61F 2/384* (2013.01); *A61F 2/3859* (2013.01); *A61F 2220/0025* (2013.01)

(58) Field of Classification Search
CPC ........ A61F 2/30734; A61F 2/38; A61F 2/389; A61F 2/3868
See application file for complete search history.

(56) References Cited

U.S. PATENT DOCUMENTS

| | | |
|---|---|---|
| 3,852,830 A | 12/1974 | Marmor |
| 3,869,729 A | 3/1975 | Attenborough |
| 3,953,899 A | 5/1976 | Charnley |
| 3,958,278 A | 5/1976 | Lee et al. |
| 4,034,418 A | 7/1977 | Jackson et al. |
| 4,215,439 A | 8/1980 | Gold et al. |
| 4,219,893 A | 9/1980 | Noiles |
| 4,224,697 A | 9/1980 | Murray et al. |
| 4,340,978 A | 7/1982 | Buechel et al. |
| 4,790,853 A | 12/1988 | Engelbrecht et al. |
| 4,838,891 A | 6/1989 | Branemark et al. |
| 5,011,496 A | 4/1991 | Forte et al. |

(Continued)

FOREIGN PATENT DOCUMENTS

| | | |
|---|---|---|
| DE | 2901009 A1 | 7/1980 |
| DE | 3343606 A1 | 7/1985 |

(Continued)

OTHER PUBLICATIONS

Extended European Search Report, European Application No. 20152508.6, dated Jun. 9, 2020, 7 pages.

(Continued)

*Primary Examiner* — Jason-Dennis N Stewart
(74) *Attorney, Agent, or Firm* — Barnes & Thornburg LLP

(57) ABSTRACT

An orthopaedic prosthesis includes a femoral component configured to be attached to a distal end of a patient's femur. A tibial tray is configured to be attached to a proximal end of a patient's tibia. A tibial insert is configured to rotate relative to the tibial tray. A modular insert is received in a cavity defined in the tibial insert. The femoral component is rotatably coupled to the body of the modular insert.

20 Claims, 10 Drawing Sheets

(56) References Cited

U.S. PATENT DOCUMENTS

| | | | |
|---|---|---|---|
| 5,314,481 A | 5/1994 | Bianco | |
| 5,370,701 A | 12/1994 | Finn | |
| 5,413,607 A | 5/1995 | Engelbrecht et al. | |
| 5,766,257 A | 6/1998 | Goodman et al. | |
| 5,824,096 A | 10/1998 | Pappas et al. | |
| 5,824,102 A | 10/1998 | Buscayret | |
| 5,871,541 A | 2/1999 | Gerber | |
| 5,951,603 A | 9/1999 | O'Neil et al. | |
| 5,954,770 A | 9/1999 | Schmotzer et al. | |
| 6,019,794 A | 2/2000 | Walker | |
| 6,074,424 A | 6/2000 | Perrone et al. | |
| 6,117,175 A | 9/2000 | Bosredon | |
| 6,210,444 B1 | 4/2001 | Webster et al. | |
| 6,264,696 B1 | 7/2001 | Reigner et al. | |
| 6,319,283 B1 | 11/2001 | Insall et al. | |
| 6,482,209 B1 | 11/2002 | Engh et al. | |
| 6,485,519 B2 | 11/2002 | Meyers et al. | |
| 6,488,711 B1 | 12/2002 | Grafinger | |
| 6,652,587 B2 | 11/2003 | Felt et al. | |
| 6,660,039 B1 | 12/2003 | Evans et al. | |
| 6,709,461 B2 | 3/2004 | O'Neil et al. | |
| 6,723,102 B2 | 4/2004 | Johnson et al. | |
| 6,743,258 B1 | 6/2004 | Keller | |
| 6,755,864 B1 | 6/2004 | Brack et al. | |
| 6,764,516 B2 | 7/2004 | Pappas | |
| 6,770,097 B2 | 8/2004 | Leclercq | |
| 6,773,461 B2 | 8/2004 | Meyers et al. | |
| 6,827,739 B2 | 12/2004 | Griner et al. | |
| 6,972,039 B2 | 12/2005 | Metzger et al. | |
| 6,984,249 B2 | 1/2006 | Keller | |
| 7,115,131 B2 | 10/2006 | Engh et al. | |
| 7,232,465 B2 | 6/2007 | Keller | |
| 7,303,586 B2 | 12/2007 | Keller | |
| 7,326,252 B2 | 2/2008 | Otto et al. | |
| 7,572,292 B2 | 8/2009 | Crabtree et al. | |
| 7,591,855 B2 | 9/2009 | Keller | |
| 7,615,081 B2 | 11/2009 | Justin et al. | |
| 7,658,767 B2 | 2/2010 | Wyss | |
| 9,452,054 B2 | 9/2016 | Vicatos | |
| 2001/0003803 A1 | 6/2001 | Leclercq | |
| 2001/0018615 A1 | 8/2001 | Biegun et al. | |
| 2001/0021877 A1 | 9/2001 | Biegun et al. | |
| 2001/0034554 A1 | 10/2001 | Pappas | |
| 2001/0034555 A1 | 10/2001 | Pappas | |
| 2002/0058997 A1 | 5/2002 | O'Connor et al. | |
| 2002/0103541 A1 | 8/2002 | Meyers et al. | |
| 2002/0120340 A1 | 8/2002 | Metzger et al. | |
| 2002/0138150 A1 | 9/2002 | Leclercq | |
| 2002/0156535 A1 | 10/2002 | Pappas | |
| 2002/0183850 A1 | 12/2002 | Felt et al. | |
| 2003/0009228 A1 | 1/2003 | Meyers et al. | |
| 2003/0009229 A1 | 1/2003 | Pappas | |
| 2003/0009230 A1 | 1/2003 | Gundlapalli et al. | |
| 2003/0009231 A1 | 1/2003 | Gundlapalli et al. | |
| 2003/0171815 A1 | 9/2003 | Kana et al. | |
| 2003/0208276 A1 | 11/2003 | Berelsman et al. | |
| 2004/0006393 A1 | 1/2004 | Burkinshaw | |
| 2004/0039450 A1 | 2/2004 | Griner et al. | |
| 2004/0054416 A1 | 3/2004 | Wyss et al. | |
| 2004/0083003 A1 | 4/2004 | Wasielewski | |
| 2004/0102851 A1 | 5/2004 | Saladino | |
| 2004/0102852 A1 | 5/2004 | Johnson et al. | |
| 2004/0162620 A1 | 8/2004 | Wyss | |
| 2004/0186584 A1 | 9/2004 | Keller | |
| 2004/0215345 A1 | 10/2004 | Perrone, Jr. et al. | |
| 2004/0220676 A1 | 11/2004 | Keller | |
| 2004/0225368 A1 | 11/2004 | Plumet et al. | |
| 2005/0027365 A1 | 2/2005 | Burstein et al. | |
| 2005/0107883 A1 | 5/2005 | Goodfried et al. | |
| 2005/0107886 A1 | 5/2005 | Crabtree et al. | |
| 2005/0246028 A1 | 11/2005 | Pappas et al. | |
| 2006/0265078 A1 | 11/2006 | McMinn | |
| 2007/0078517 A1 | 4/2007 | Engh et al. | |
| 2008/0021566 A1 | 1/2008 | Peters et al. | |
| 2008/0058945 A1 | 3/2008 | Hajaj et al. | |
| 2009/0005875 A1 | 1/2009 | Koenemann | |
| 2009/0299482 A1 | 12/2009 | Metzger et al. | |
| 2009/0319048 A1 | 12/2009 | Shah et al. | |
| 2010/0174378 A1 | 7/2010 | Metzger et al. | |
| 2017/0312087 A1 | 11/2017 | Faccioli et al. | |

FOREIGN PATENT DOCUMENTS

| | | | |
|---|---|---|---|
| DE | 19823325 C1 | 3/2000 | |
| EP | 716839 A1 | 6/1996 | |
| EP | 724868 A1 | 8/1996 | |
| EP | 1099430 A1 | 5/2001 | |
| EP | 1721584 A1 | 11/2006 | |
| FR | 2589720 A1 | 5/1987 | |
| FR | 2601873 A1 | 1/1988 | |
| FR | 2612767 A1 | 9/1988 | |
| FR | 2760352 A1 | 9/1998 | |
| FR | 2776919 A1 | 10/1999 | |
| WO | 8702883 A1 | 5/1987 | |
| WO | 0113825 A1 | 3/2001 | |
| WO | 0217821 A2 | 3/2002 | |

OTHER PUBLICATIONS

FDA Document, KA-012255, Richards Mod II Knee, 56 pgs, 1976.

"Richards Modular Knee System", Richards Orthopedic catalog, 15 pgs, 1979.

"The femoropatellar endoprosthesis—still of value today?", Fink et al., Z Orthop Ihre Grenzgeb., May/Jun. 1999; 137 (3):247-52.

"Bicondylar St. George Sledge Knee Arthoplasty", Stockley et al., Clinical Orthopaedics and Related Research, No. 255, Jun. 1990, pp. 228-233.

"New Jersey Low Contact Stress Knee Replacement System", Buechel and Pappas, Surgical Reconstruction of the Arthritic Knee II, 1989.

"Patellofemoral Arthroplasty: A Three-to-Nine-Year Follow-up Study", Arciero et al, Clinical Orthopaedics and Related Research, No. 236, Nov. 1988, pp. 60-71.

"Kinematic I and Oxford Knee Arthroplasty—A 5-8-year FollowUp Study", Bourne et al., The Journal of Arthroplasty No. 4, Dec. 1987, pp. 285-291.

"Failed Polycentric Total Knee Prosthesis", Shoji et al., vol. 58-A, The Journal of Bone and Joint Surgery, No. 6, Sep. 1976, pp. 773-777.

ORTHOPAEDIC PROSTHETIC SYSTEM FOR A ROTATING HINGED-KNEE PROSTHESIS

TECHNICAL FIELD

The present disclosure relates generally to an orthopaedic prosthesis system, including prosthetic components and methods for assembling the prosthetic components during an orthopaedic joint replacement procedure, and, more particularly, to orthopaedic prosthetic components and methods for assembling the prosthetic components during a knee replacement procedure.

BACKGROUND

Movement (e.g., flexion and extension) of the natural human knee involves movement of the femur and the tibia. Specifically, during flexion and extension, the distal end of the femur and the proximal end of the tibia articulate relative to one another through a series of complex movements. Damage (e.g., trauma) or disease can deteriorate the bones, articular cartilage, and ligaments of the knee, which can ultimately affect the ability of the natural knee to function in such a manner. As a result, knee prostheses have been developed and implanted into surgically-prepared ends of the femur and tibia.

A typical knee prosthesis for a total knee replacement, for example, includes a tibial component or tibial tray coupled to the patient's tibia, a femoral component coupled to the patient's femur, and a tibial insert component positioned between the tibial tray and the femoral component and including a surface to accommodate the condyles of the femoral component. One type of knee prosthesis is a hinged knee prosthesis, which typically includes a hinge mechanism to couple the femoral component to one or both of the bearing component and the tibial components in order to constrain and mechanically link the components of the knee prosthesis together.

SUMMARY

According to one aspect of the disclosure, an orthopaedic prosthesis includes a femoral component configured to be attached to a distal end of a patient's femur. A tibial tray is configured to be attached to a proximal end of a patient's tibia. The tibial tray includes a base having an outer surface, a post extending distally from the base, and an aperture extending defined in the post and the base. A tibial insert is configured to rotate relative to the tibial tray. The tibial insert includes a platform shaped to engage the base of the tibial tray. A stem extends distally from the platform and is received in the aperture of the tibial tray. A cavity extends longitudinally through the platform. A tab is coupled to the platform. The tab is configured to engage the outer surface of the base to limit rotation of the tibial insert relative to the tibial tray. A modular insert is received in the cavity defined in the tibial insert. The modular insert includes an elongated stem, and a body rotatably coupled to the elongated stem. The femoral component is rotatably coupled to the body of the modular insert. The femoral component is configured to rotate about a first axis relative to the tibial insert over a first range of motion. The first axis extends in a medial-lateral direction. The body of the modular insert is configured to rotate relative to the tibial insert about a second axis extending parallel to the first axis over a second range of motion. The second range of motion is less than the first range of motion.

In some embodiments, the body of the modular insert may be configured to rotate relative to the femoral component to move the first axis relative to the second axis over the second range of motion.

In some embodiments, an elongated pin may connect the femoral component to the body of the modular insert. The elongated pin may define the first axis and may be moveable between a first position and a second position relative to the tibial insert over the second range of motion. The second position may be located anterior of the first position. The modular insert may be configured to move in a superior-inferior direction relative to the tibial insert over the second range of motion between an inferior position and a superior position. When the modular insert is positioned in the inferior position, the elongated pin may be in the first position. When the modular insert is positioned in the superior position, the elongated pin may be in the second position. The tibial insert may have an inner wall that defines the cavity. The inner wall may have a tapered proximal surface that defines a proximal section of the cavity. The body of the modular insert may be seated in the proximal cavity section when the modular insert is positioned in the inferior position. The inner wall of the tibial insert may have an inferior base surface. The tapered proximal surface of the tibial insert may extend from an elongated opening defined in the platform to the inferior base surface.

In some embodiments, the elongated opening may have a substantially oval shape. An opening may be defined in the inferior base surface. The inner wall of the tibial insert may have a distal surface that defines a distal section of the cavity. The elongated stem of the modular insert may extend into the distal cavity section. The elongated stem of the modular insert may define a longitudinal axis. The modular insert may be permitted to rotate about the longitudinal axis relative to the tibial insert when the modular insert is positioned in the superior position.

In some embodiments, the tab may be removably coupled to the platform of the tibial insert.

In some embodiments, the first range of motion may be in a range of −3 to 140 degrees of flexion. The second range of motion may be in a range of 3 to 10 degrees of flexion.

According to another aspect of the disclosure, an orthopaedic prosthesis system includes a first implantable prosthetic component that is configured to be attached to a distal end of a patient's femur. The first implantable prosthetic component includes a first body having a pair of spaced apart curved convex condyle surfaces. A second body is rotatably coupled to the first body. An elongated stem is rotatably coupled to the second body. A second implantable prosthetic component is configured to be attached to a proximal end of a patient's tibia. An insert prosthetic component is configured to be positioned between the first implantable prosthetic component and the second implantable prosthetic component. The insert prosthetic component includes a cavity sized to receive the elongated stem of the first implantable prosthetic component. The first body is configured to rotate about a first axis relative to the insert prosthetic component over a first range of motion. The first axis extends in a medial-lateral direction. The second body is configured to rotate relative to the insert prosthetic component about a second axis extending parallel to the first axis over a second range of motion. The second range of motion is less than the first range of motion.

In some embodiments, an elongated pin may connect the first body to the second body. The elongated pin may define the first axis and may be moveable between a first position and a second position relative to the insert prosthetic component over the second range of motion. The second position may be located anterior of the first position. The second body of the first implantable prosthetic component may be configured to move in a superior-inferior direction relative to the insert prosthetic component over the second range of motion between an inferior position and a superior position. When the second body is positioned in the inferior position, the elongated pin may be in the first position. When the second body is positioned in the superior position, the elongated pin may be in the second position. The insert prosthetic component may have a pair of curved proximal surfaces. The pair of spaced apart curved convex condyle surfaces of the first body may be configured to engage the curved proximal surfaces. The curved convex condyle surfaces and the curved proximal surfaces may be shaped such that the engagement of curved convex condyle surfaces and the curved proximal surfaces over the second range of motion causes the second body of the first implantable prosthetic component to move between the inferior position and the superior position.

In some embodiments, the second range of motion may overlaps with the first range of motion. The first range of motion may be in a range of −3 to 140 degrees of flexion. The second range of motion may be in a range of 3 to 10 degrees of flexion.

According to yet another aspect of the disclosure, an orthopaedic prosthesis system includes a first implantable prosthetic component that is configured to be attached to a distal end of a patient's femur and includes a pair of spaced apart curved convex condyle surfaces. A second implantable prosthetic component is configured to be attached to a proximal end of a patient's tibia. An insert prosthetic component is positioned between the first implantable prosthetic component and the second implantable prosthetic component. The insert prosthetic component includes a pair of curved proximal surfaces engaged with the pair of spaced apart curved convex condyle surfaces. An elongated pin extends along a first axis. The elongated pin rotatably couples the insert prosthetic component to the first implantable prosthetic component. The first implantable prosthetic component is configured to rotate about the first axis relative to the insert prosthetic component over a range of motion. The first axis extends in a medial-lateral direction. The curved convex condyle surfaces and the curved proximal surfaces are shaped such that the engagement of curved convex condyle surfaces and the curved proximal surfaces over the range of motion causes the elongated pin to move between a first position and a second position. The second position is located anterior of the first position.

BRIEF DESCRIPTION OF THE DRAWINGS

The detailed description particularly refers to the following figures, in which.

DETAILED DESCRIPTION OF THE DRAWINGS

Figure 1:
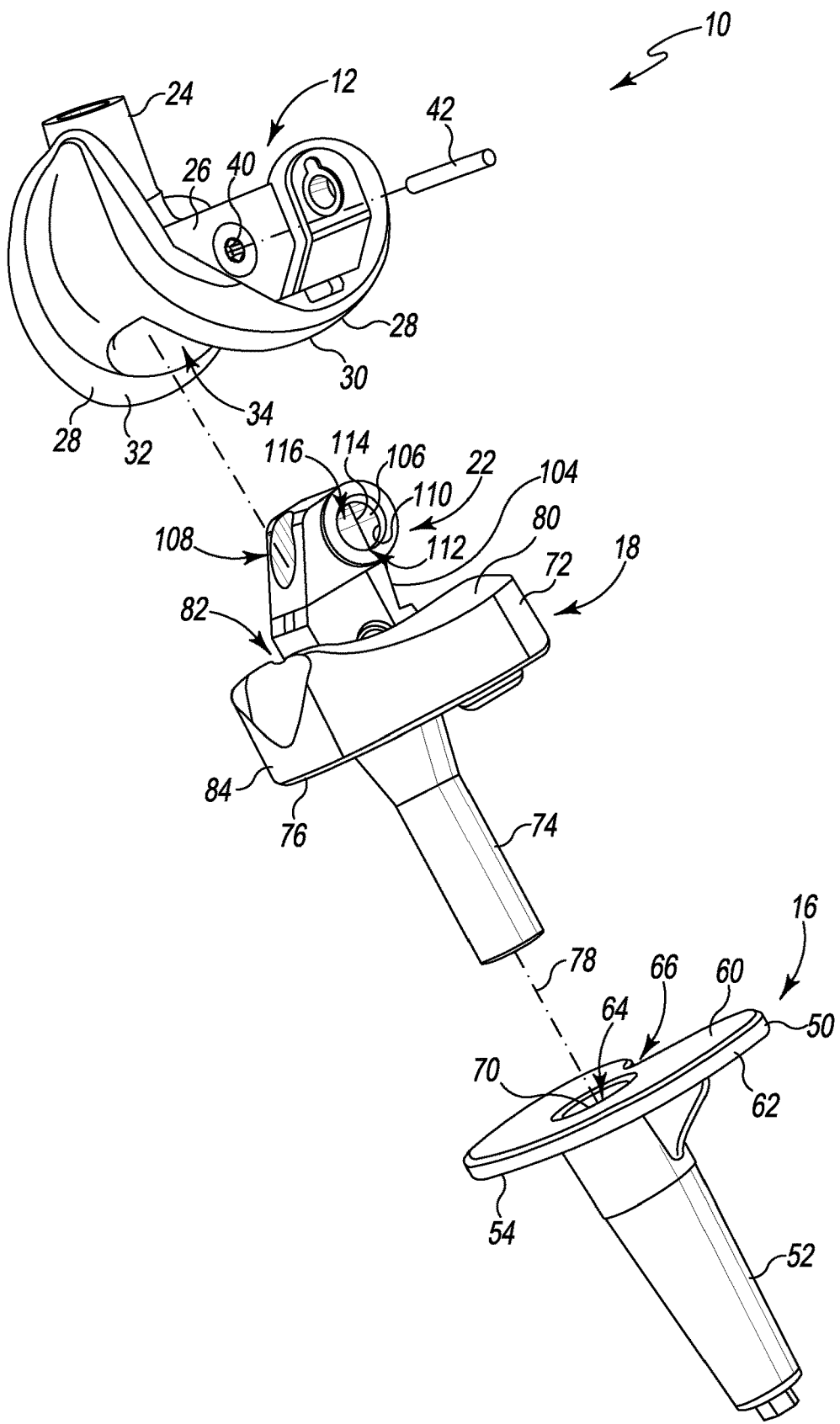
FIG. 1 is an exploded view of an orthopaedic knee prosthesis system.

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the invention as defined by the appended claims.

Terms representing anatomical references, such as anterior, posterior, medial, lateral, superior, inferior, etcetera, may be used throughout the specification in reference to the orthopaedic implants and orthopaedic surgical instruments described herein as well as in reference to the patient's natural anatomy. Such terms have well-understood meanings in both the study of anatomy and the field of orthopaedics. Use of such anatomical reference terms in the written description and claims is intended to be consistent with their well-understood meanings unless noted otherwise.

Referring now to FIG. 1, an orthopaedic knee prosthesis system 10 is shown. The orthopaedic knee prosthesis system 10 includes a femoral component 12 configured to be coupled to a distal end of a patient's femur, a tibial tray 16 that is configured to be coupled to a proximal end of a patient's femur, and a tibial insert 18 configured to be assembled separately with the tibial tray 16. The femoral component 12, the tibial tray 16, the tibial insert 18, and a modular insert 22 may be separately assembled to form an orthopaedic knee prosthesis; specifically, a hinged orthopaedic knee prosthesis, as described below.

The system 10 is configured to articulate through three ranges of motion. The system 10 moves through various degrees of flexion between full extension and full flexion. As the system 10 articulates through a range of flexion a contact point between condyles of the femoral component 12 and condyle surfaces of the tibial insert 18 moves so that the contact point is different at different degrees of flexion. Additionally, the surgeon can selectively add rotation about a superior-inferior axis. The rotation may occur between the femoral component 12 and the tibial insert 18. The rotation may also occur between the tibial insert 18 and the tibial tray 16. As the system moves to within a first range of flexion, the contact point between the condyles and the condyle surfaces moves in an anterior-posterior direction. During a second range of flexion that is within the first range of flexion, the femoral component 12 may be permitted to rotate relative to the tibial insert 18. In some embodiments, the surgeon may also selectively permit the tibial insert 18 to rotate relative to the tibial tray 16 throughout the first range of flexion. An amount of rotation of the tibial insert 18 relative to the tibial tray 16 may be adjusted by the surgeon.

In the illustrative embodiment, the femoral component 12 includes a post 24 that is configured to be implanted into the distal end of the patient's femur. The post 24 is attached to a body 26 having a pair of spaced-apart lateral and medial condyles 28. The condyles 28 include respective lateral and medial condyle surfaces 30, 32, which are curved convexly. An intercondylar notch 34 is defined between the lateral and medial condyles 28 and is sized to receive the modular insert 22. The femoral component 12 also includes a posterior bore 40 that extends in a medial-lateral direction through the lateral and medial condyles 28. As described in greater detail below, the bore 40 forms part of the hinge mechanism and is sized to receive a hinge pin 42.

The femoral component 12 and the tibial tray 16 are each formed from an implant grade metallic material such as, for example, cobalt chromium. As shown in FIG. 1, the tibial tray 16 includes a base 50 and an anchor 52 that extends inferiorly from a distal surface 54 of the base 50. The base 50 is sized and shaped to conform to the configuration of a surgically-prepared proximal surface of the patient's tibia, and the anchor 52 is sized and shaped to be implanted into a surgically-prepared intramedullary canal of the patient's tibia.

The base 50 includes a substantially planar proximal surface 60 that is positioned opposite the distal surface 54. A curved outer wall 62 extends between from the surfaces 54, 60 and is sized and shaped to conform to the outer edge of the surgically-prepared proximal surface of the patient's tibia. A concave posterior-facing channel 66 is formed by the outer wall 62. An opening 64 is defined in the proximal surface 60, and the tray 16 includes an aperture 70 that extends inwardly from the opening 64. The aperture 70 extends through the base 50 and into the anchor 52.

The tibial tray 16 may be assembled with the tibial insert 18 shown in FIG. 1 to form a tibial component. The insert is formed from an implant grade plastic material such as, for example, ultra-high molecular weight polyethylene (UHMWPE). The tibial insert 18 includes a platform 72 that is sized to be positioned on the proximal surface 60 of the tibial tray 16 and an elongated stem 74 that extends inferiorly from a distal surface 76 of the platform 72 along a longitudinal axis 78 that extends in an inferior-superior direction. Similar to the proximal surface 60 of the tibial tray 16, the distal surface 76 of the platform is substantially planar. The platform 72 also includes a pair of concave curved proximal surfaces 80, 82 that correspond to the lateral and medial condyle surfaces 30, 32 of the femoral component 12. The platform 72 also includes a curved outer wall 84 that extends between the surfaces 80, 82.

Figure 2:
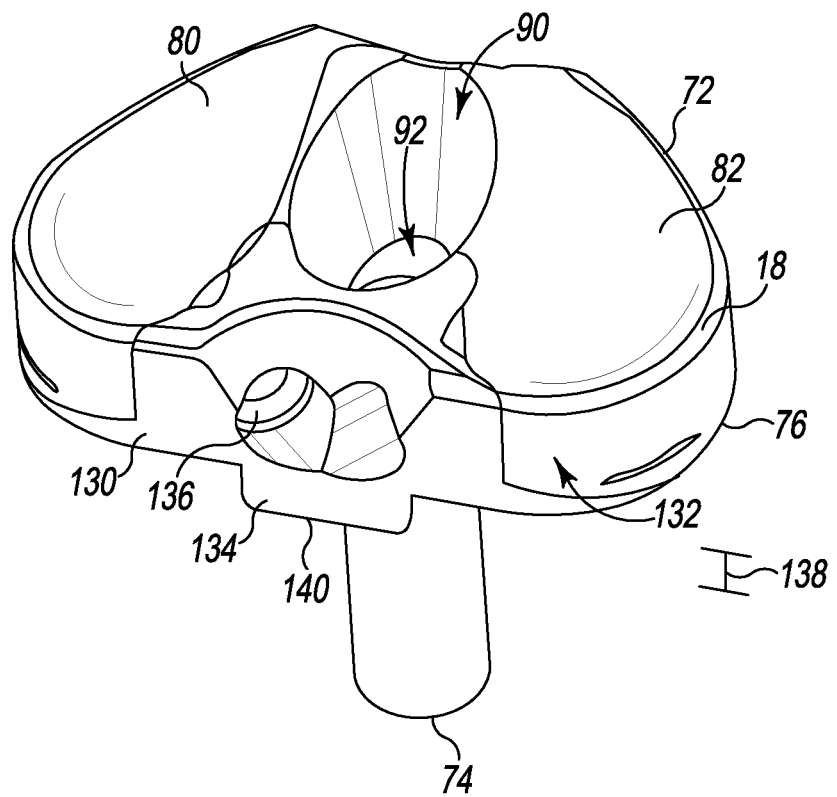
FIG. 2 is a top perspective view of the tibial insert shown in FIG. 1 and a posterior insert coupled to the tibial insert.

Referring now to FIG. 2, an opening 90 is defined in the proximal surfaces 80, 82 of the platform 72. The tibial insert 18 includes an aperture 92 that extends inwardly from the opening 90 through the platform 72 and into the elongated stem 74. The aperture 92 then extends along the longitudinal axis 78 of the stem 74.

When coupled to the tibial tray 16, the distal surface 76 of the tibial insert 18 engages the proximal surface 60 of the tibial tray. The elongated stem 74 of the tibial insert 18 is sized to be received in the aperture 70 of the tibial tray 16 when the tibial insert 18 is coupled to the tibial tray.

Referring back to FIG. 1, the modular insert 22 includes an elongated stem 100 (shown in FIG. 8) that extends along the longitudinal axis 78. A proximal body 104 is pivotally attached to the stem 100. The stem 100 is sized and shaped to be inserted in the opening 90, and extend into the aperture 92, of the tibial insert 18. The proximal body 104 includes a medial opening 106, a lateral opening 108, and an inner wall 110 extending between the medial opening 106 and the lateral opening 108. The inner wall 110 defines a cylindrical pin hole 112 that extends through the proximal body 104.

The proximal body 104 of the modular insert is sized and shaped to be positioned within the intercondylar notch 34 of the femoral component 12 such that the posterior bore 40 may be aligned with the passageway 116 of the modular insert 22. The hinge pin 42 extends through the posterior bore 40 and the passageway 116 along a longitudinal axis 20 that extends in a medial-lateral direction to attach the modular insert 22 to the femoral component 12. As described above, the tibial tray 16 and the tibial insert 18 may be combined with the femoral component 12 and the modular insert 22 to form a hinged orthopaedic knee prosthesis.

Figure 3:
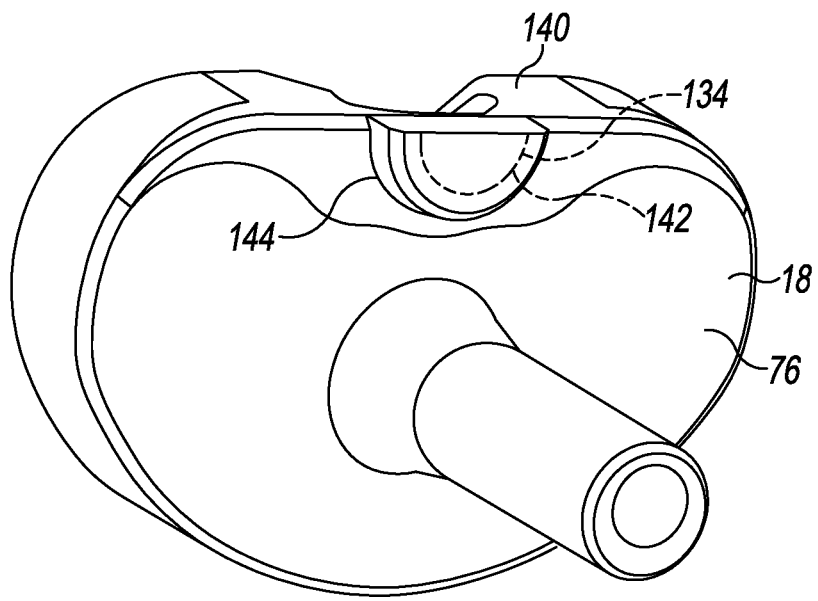
FIG. 3 is a bottom perspective view of the tibial insert shown in FIG. 2.

Referring to FIGS. 2 and 3, a posterior component 130 is removably coupled to a posterior side 132 of the platform 72 of the tibial insert with fasteners 136. The posterior component 130 limits an amount of rotation between the tibial insert 18 and the tibial tray 16. In some embodiments, a plurality of posterior components 130 may be provided, wherein each posterior component 130 provides a different predetermined amount of rotation between the tibial insert 18 and the tibial tray 16. In some embodiments, a posterior component 130 may be provided to completely prevent rotation between the tibial insert 18 and the tibial tray 16. The posterior component 130 includes an inferiorly-extending tab 134 extending from a surface of the posterior component 130. The tab 134 extends from the distal surface 76 of the tibial insert 18 when the posterior component 130 is coupled to the tibial insert 18. In some embodiments, the posterior component 130 is formed integrally with the tibial insert 18. The tab 134 extends a length 138 from the distal surface 76. The tab 134 includes a planar side wall 140 extending along the posterior side 132 of the tibial insert 18. A curved convex side wall 142 extends in an anterior direction from the planar side wall 140. The curved side wall 142 extends below the distal surface 76 of the tibial insert 18.

The curved side wall 142 is sized to be positioned within the channel 66 of the tibial tray 16. The curved side wall 142 is sized smaller than the channel 66 so that the tibial insert 18 is permitted to rotate relative to the tibial tray 16, as described in more detail below. In other embodiments, the tab 134 of the different posterior component 130 includes a curved side wall 144 (shown in broken lines) that is sized to be secured within the channel 66 to prevent rotation of the tibial insert 18 relative to the tibial tray 16, as described in greater detail below. As noted above, the system 10 may include multiple posterior components 130 having different sized tabs 134. Accordingly, the surgeon can select a tab size based on a preferred amount of rotation. In some embodiments the tibial tray 16 rotates in increments of 5 degrees from 0 to +/−20 degrees.

Figure 4:
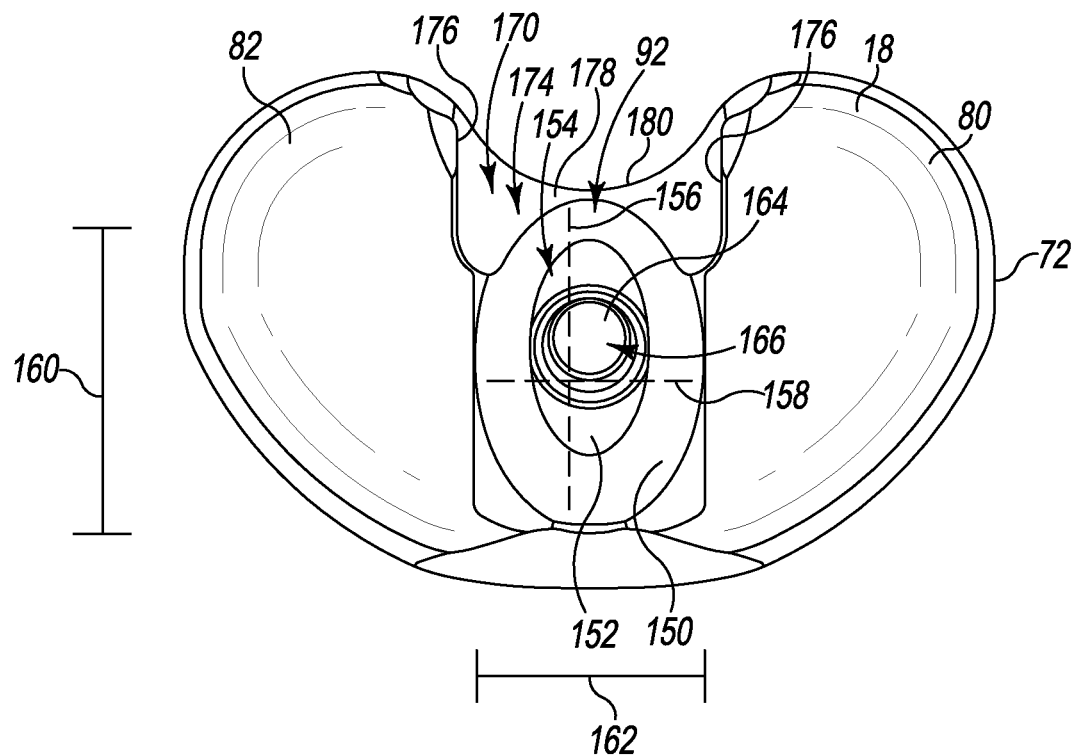
FIG. 4 is a top plan view of the tibial insert shown in FIG. 2 with the posterior insert removed.
Figure 5:
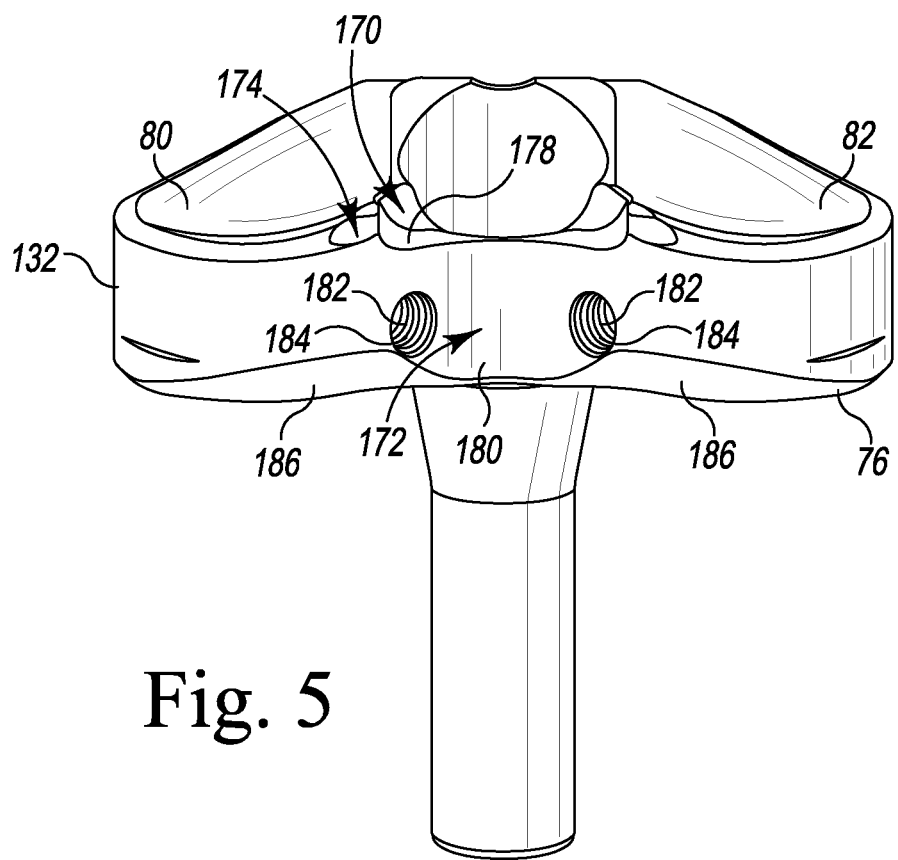
FIG. 5 is a rear perspective view of the tibial insert shown in FIG. 4.

As illustrated in FIGS. 4 and 5, the tibial insert 18 includes a mounting cavity 168 that extends from a superior opening 170 formed in the proximal surfaces 80, 82 and an opening 172 formed in the posterior side 132. The mounting cavity 168 is sized to receive the posterior component 130, when the posterior component 130 is coupled to the tibial insert 18. A cavity 174 extends from the openings 170 and 172 and is sized to receive the posterior component 130. The cavity 174 includes a pair of posterior planar side walls 176 extending from the superior opening 170 to a bottom wall 178. A curved end wall 180 extends from the bottom wall 178 to the distal surface 76 of the tibial insert 18. A pair of openings 182 is formed in the curved end wall 180. A bore 184 extends from each opening 182 into the tibial insert 18. Curved notches 186 extend medially and laterally from the curved end wall 180 along the posterior side 132 of the tibial insert 18.

Figure 6:
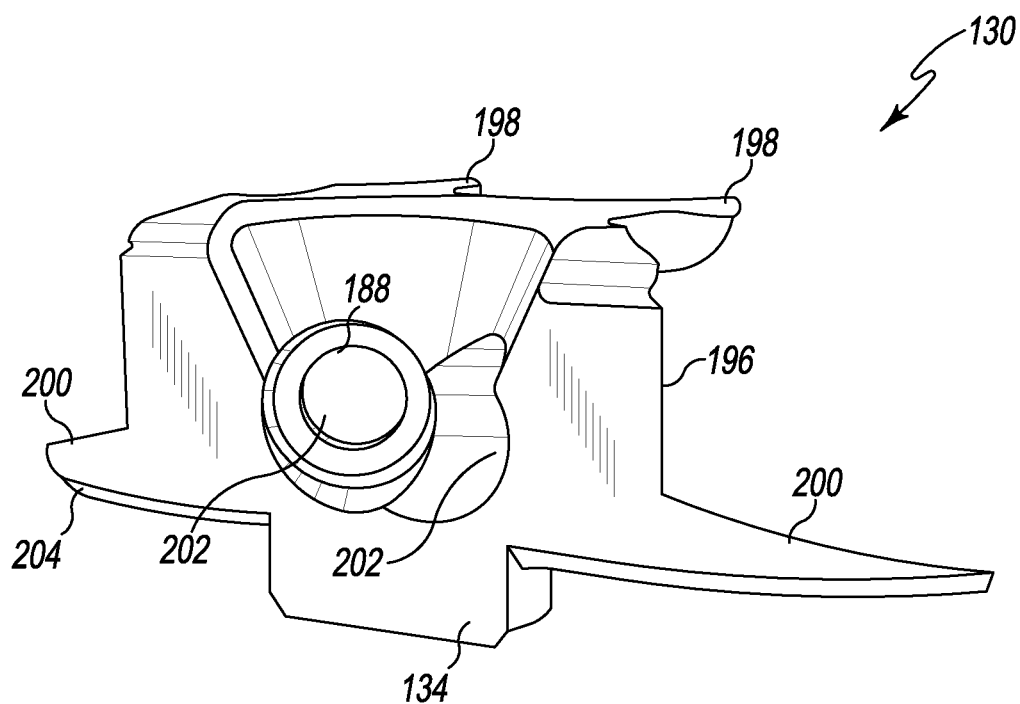
FIG. 6 is a rear perspective view of the posterior insert shown in FIG. 2.

Referring now to FIG. 6, the posterior component 130 includes a body 196. The tab 134 extends inferiorly from the body 196. A pair of upper flanges 198 extends in an anterior direction from the body 196. The upper flanges 198 are sized and shaped to be received in the proximal cavity 154 of the tibial insert 18. A pair of lower flanges 200 extends medially and laterally from the body 196. Each of the pair of lower flanges 200 is sized and shaped to position in a respective curved notch 186 of the tibial insert 18.

A pair of openings 202 is formed in a posterior end 204 of the body 196. A bore 188 extends inward from each of the pair of openings 202 through the body 196 of the posterior component 130. The bores 188 are configured to align with the bores 174 of the tibial insert 18 when the posterior component 130 is coupled to the tibial insert 18. The fasteners 136 are received in the bores 174 and the bores 188 to secure the posterior component 130 to the tibial insert 18. In some embodiments, the bores 138 and 174 are threaded to receive a threaded fastener 136.

Figure 7:
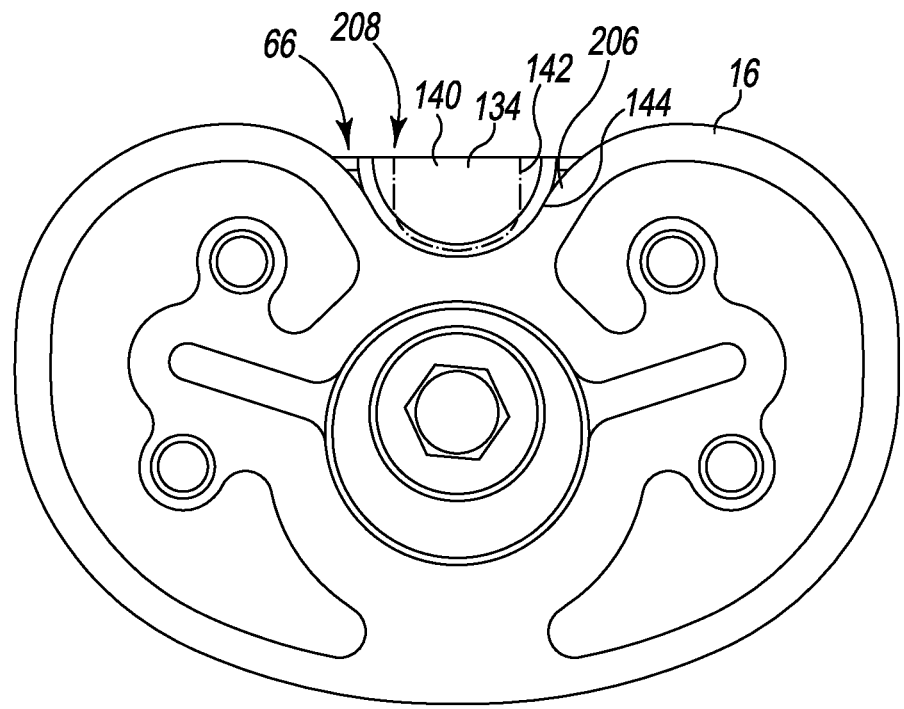
FIG. 7 is a bottom plan view of the tibial tray shown in FIG. 1 and the tibial insert shown in FIG. 1 coupled to the tibial tray.

FIG. 7 illustrates the tab 134 of the posterior component 130 extending into the channel 66 of the tibial tray 16 when the tibial insert 18 is coupled to the tibial tray 16. The channel 66 of the tibial tray 16 includes a curved side wall 206 extending from an opening 208 having a length 210. The tab 134 is sized so that the planar side wall 140 has a length less than the length 210 of the opening 208. Also, the curved side wall 142 of the tab 134 is sized to be smaller than the curved side wall 206 of the channel 66 to permit movement of the tab 134 within the channel 66. A combination of the size of the planar side wall 140 and the size of the curved side wall 142 relative to the size of the channel 66 permits limited rotation of the tibial insert 18 relative to the tibial tray 16. That is, the tibial insert 18 is permitted to rotate about the longitudinal axis 78 until the curved side wall 142 of the tab 134 contacts the curved side wall 206 of the channel 66.

In another embodiment, the tab 134 includes curved side wall 144. In such an embodiment, the planar side wall 140 has a length 212 that is substantially equal to the length 210 of the opening 208. Additionally, the curved side wall 144 of the tab 134 is sized to contact the curved side wall 206 of the channel 66 to prevent rotation of the tibial insert 18 relative to the tibial tray 16.

Referring back to FIG. 4, the aperture 92 of the tibial insert 18 includes a tapered inner wall 150 extending from the platform 72 to an inferior base wall 152 to define a proximal cavity 154 extending longitudinally through the platform 72. The inner wall 150 is sloped radially inward from the platform 72 to the inferior base wall 152. The inner wall 150 is substantially oval in shape so that the proximal cavity 154 includes a major axis 156 extending in the anterior-posterior direction and a minor axis 158 extending in the medial-lateral direction. The major axis 156 has a length 160 that is greater than a length 162 of the minor axis 158. In some embodiments, the minor axis 158 extends in the anterior-posterior direction, and the major axis 156 extends in the medial-lateral direction. At the platform 72, the major axis 156 and the minor axis 158 each have a maximum length. Due to the slope of the inner wall 150, the major axis 156 and the minor axis 158 have a minimum length at the inferior base wall 152. The lengths of the major axis 156 and the minor axis 158 gradually decrease through various intermediate lengths between the platform 72 and the inferior base wall 152.

An opening 164 is formed in the inferior base wall 152. A distal cavity 166 extends from the opening 164. The distal cavity 166 is generally cylindrical in shape and extends from the opening 164 to a bottom wall 168. The distal cavity 166 is sized to receive the elongated stem 100 of the modular insert 22.

Figure 8:
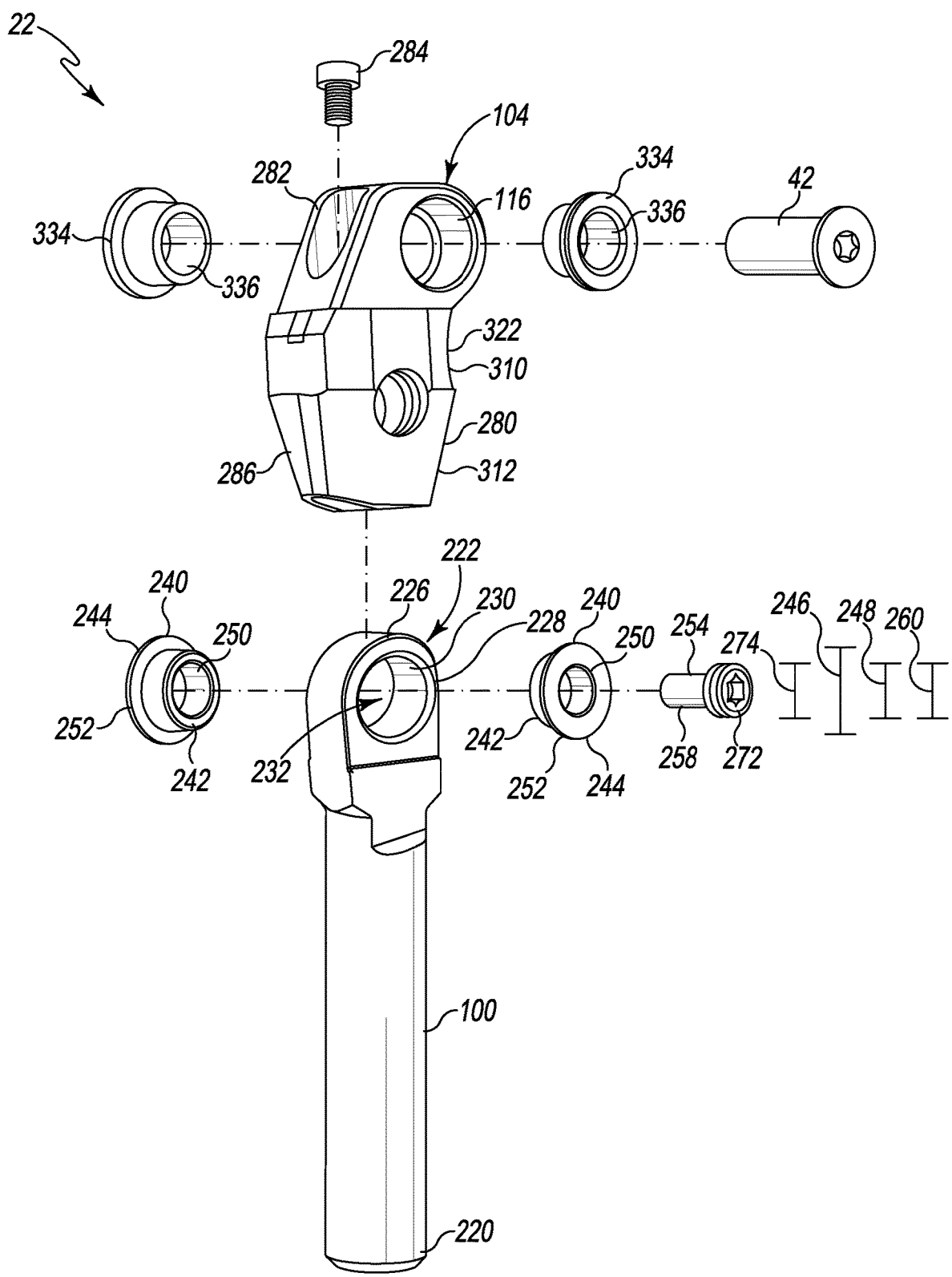
FIG. 8 is an exploded view of the modular insert shown in FIG. 1.

Referring now to FIG. 8, the elongated stem 100 of the modular insert 22 extends between a distal end 220 and a proximal end 222. The distal end 220 of the elongated stem 100 is sized to position in the distal cavity 166 of the tibial insert 18. The proximal end 222 includes a rounded outer wall 226 and a pair of linear side walls 228 extending from the rounded outer wall 226. A pin hole 230 extends between a pair of openings 232 formed in the proximal end 222. Each of a pair of bushings 240 is sized to be positionedbin one of the openings 232.

Each bushing 240 includes a body 242 and a flange 244 extending around the body 242. The flange 244 has a diameter 246 that is greater than a diameter 248 of the body 242. The diameter 248 of the body 242 is sized so that the body 242 positions within the opening 232. The diameter 246 of the flange 244 is sized so that the flange 244 positions against the respective side wall 228.

Each bushing 240 includes a pin hole 250 extending between a pair of openings 252. The pin hole 250 is sized to receive a pin 254 along a longitudinal axis 256 that extends parallel to the longitudinal axis 20 in a medial-lateral direction. The pin 254 includes a cylindrical shaft 258 having a diameter 260 sized to a diameter 270 of the pin hole 250. A threaded head 272 extends from the shaft 258. The threaded head 272 has a diameter 274 that is greater than the diameter 260 of the shaft 258.

The proximal body 104 of the modular insert 22 includes a distal section 280 and a spine 282 extending proximally from the distal section 280. A fastener 284 is configured to secure the spine 282 to the distal section 280. The distal section 280 is sized to position in the proximal cavity 154 of the tibial insert 18. The distal section 280 includes an outer side wall 286 that is sized and shaped to the inner wall 150 of the tibial insert 18. The outer side wall 286 is generally oval in shape and slopes from superior end 288 to an inferior end 298. The distal section 280 is configured to receive the proximal end 222 of the elongated stem 100.

Figure 9:
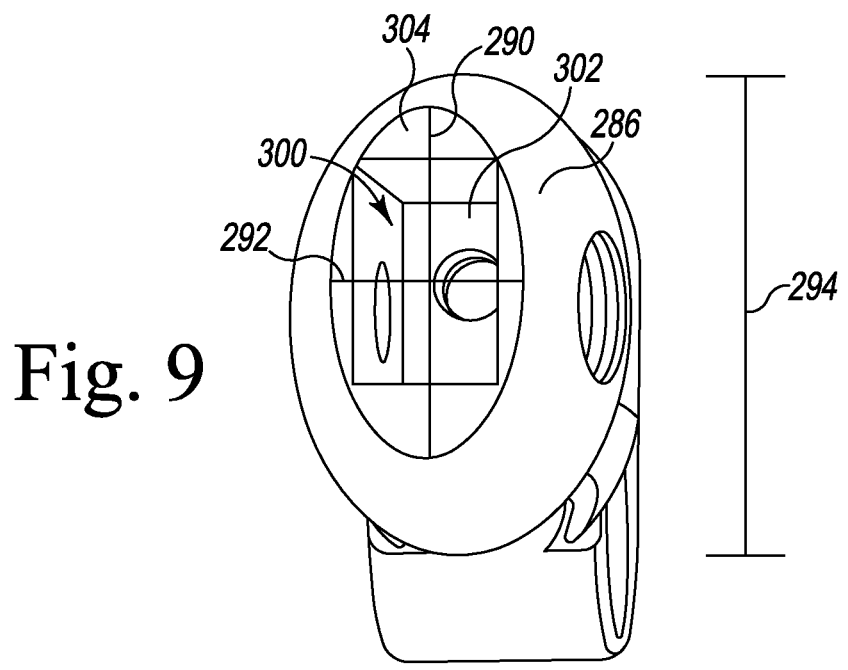
FIG. 9 is a bottom perspective view of the body of the modular insert shown in FIG. 1.

Referring now to FIG. 9, the outer side wall 286 includes a major axis 290 extending in the anterior-posterior direction and a minor axis 292 extending in the medial-lateral direction. The major axis 290 has a length 294 that is greater than a length 296 of the minor axis 292. In some embodiments, the major axis 290 extends in the medial-lateral direction and the minor axis 292 extends in the anterior-posterior direction. The distal section 280 includes a cavity 300 extending from an opening 302 in a distal end 304 of the distal section 280. The cavity 300 is sized and shaped to receive the proximal end 222 of the elongated stem 100.

At the superior end 288, the major axis 290 and the minor axis 292 each have a maximum length. Due to the slope of the outer side wall 286, the major axis 290 and the minor axis 292 have a minimum length at the inferior end 298. The lengths of the major axis 290 and the minor axis 292 gradually decrease through various intermediate lengths between the superior end 288 and the inferior end 298.

The outer side wall 286 is configured to engage the inner wall 150 of the tibial insert 18, when the modular insert 22 is coupled to the tibial insert 18. At an initial extended position, the distal section 280 of the modular insert 22 is seated in the aperture 92 of the tibial insert 18 with the inferior end 298 positioned against the inferior base wall 152 of the tibial insert 18. The outer side wall 286 is positioned against the inner wall 150 of the tibial insert 18. During flexion of the femoral component 12 relative to the tibial insert 18, the modular component 22 moves in a superior direction so that the inferior end 298 is separated from the inferior base wall 152 of the tibial insert 18. In a separated position, the axes 290, 292 of the modular insert 22 are positioned so that a length of the axes 290, 292 at any given location is less than a length of an aligned axis 156, 158. For example, the axis 156, 158 at the platform 72 are aligned with an intermediate axis 290, 292 of the modular insert 22 that has a shorter length, thereby permitting rotation of the modular insert 22 relative to the tibial insert 18.

Figure 10:
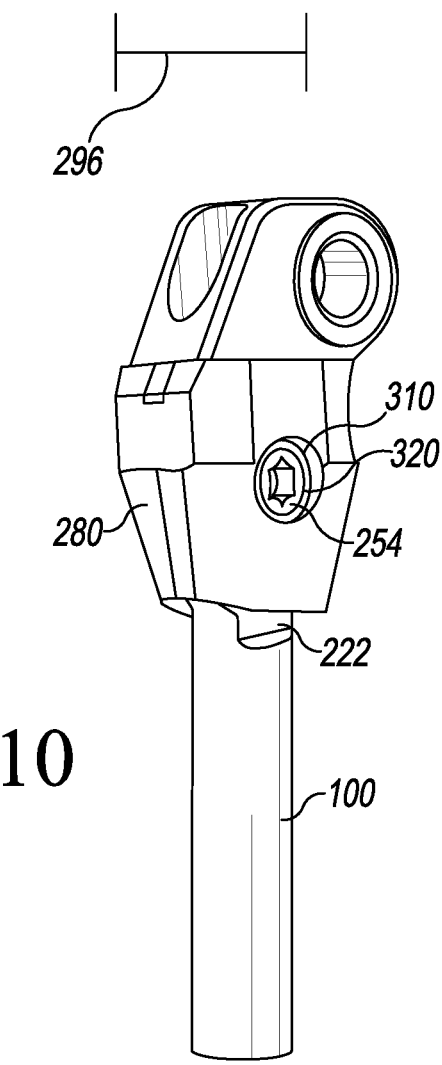
FIG. 10 is a side perspective view of the modular insert shown in FIG. 1.

Referring back to FIG. 8, a threaded bore 310 extends from openings 312 in the distal section 280 and into the cavity 300. As illustrated in FIG. 10, when the proximal end 222 of the elongated stem 100 is received in the cavity 300, the threaded bore 310 is configured to align with the pin hole 230 of the elongated stem 100 and the pin holes 250 of the bushings 240 to define a passageway 320. The passageway 320 is configured to receive the pin 254 to hingedly attach the distal section 280 to the elongated stem 100. The threaded head 272 is secured to threads 322 of the bore 310 to secure the pin 254 to the distal section 280. The proximal body 104 of the modular insert 22 is configured to rotate about the longitudinal axis 256 in the direction of arrow 324 relative to the elongated stem 100.

Figure 11:
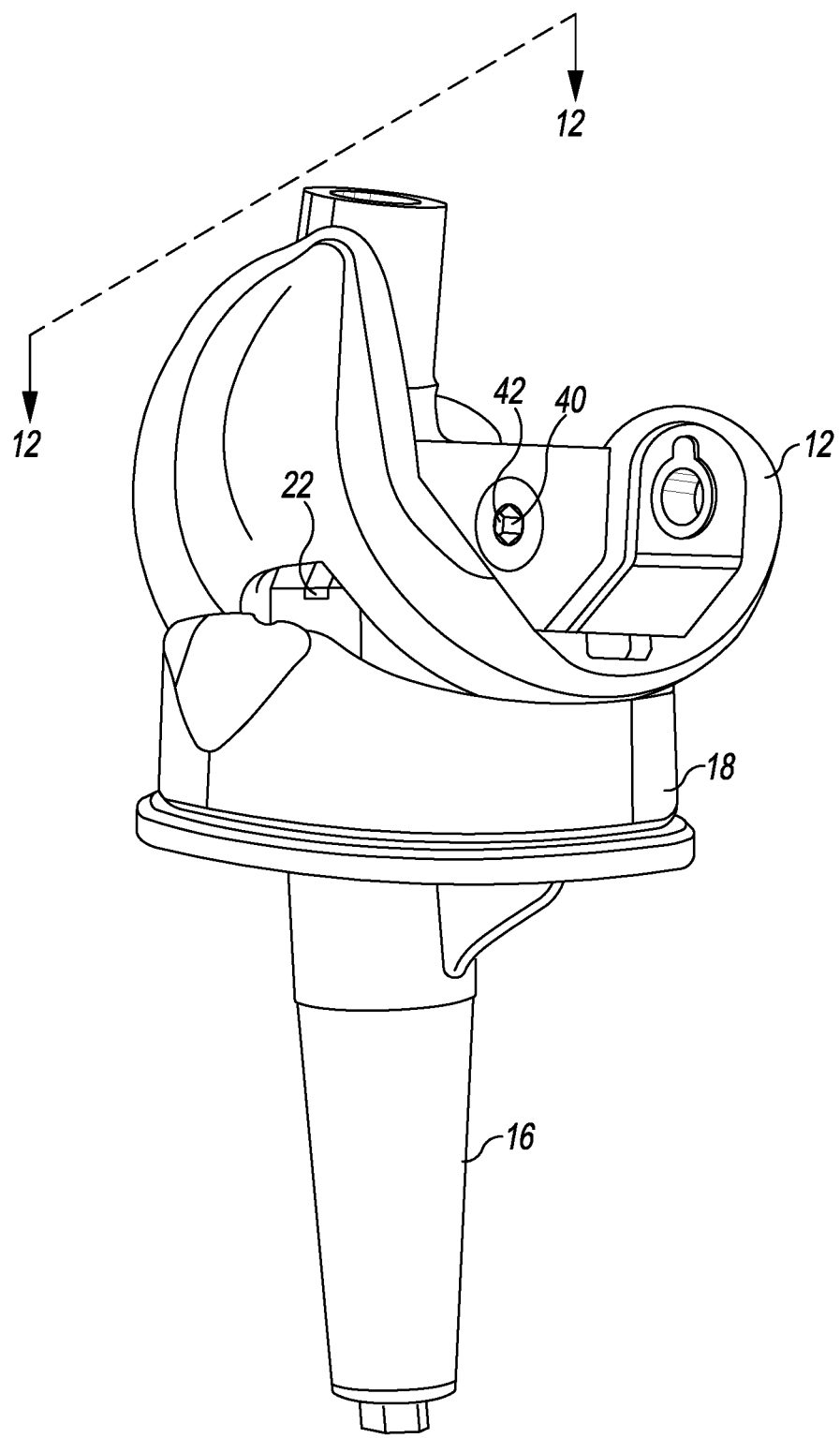
FIG. 11 is a side perspective view of the orthopaedic knee prosthesis system shown in FIG. 1.

The spine 282 of the proximal body 104 includes the passageway 116 extending between the medial opening 106 and the lateral opening 108. Each opening 106, 108 is sized and shaped to receive a bushing 334. Each bushing 334 includes a bore 336 extending between openings 338. As illustrated in FIG. 11, the bores 336 are configured to align with the posterior bore 40 of the femoral component 12, when the femoral component 12 is coupled to the modular insert 22. The hinge pin 42 extends through the posterior bore 40, the passageway 116, and the bores 336 to pivotally attach the modular insert 22 to the femoral component 12 along a longitudinal axis 20. The femoral component 12 is configured to rotate about arrow 340, when the femoral component 12 is coupled to the modular insert 22.

During an operation to replace a patient's knee, the surgeon selects a femoral component 12 and a tibial tray 16. An end of the patient's femur and an end of the patient's tibia are resected to prepare for insertion of the system 10. The surgeon drills intramedullary canals in the femur and the tibia to receive the post 24 of the femoral component 12 and the stem 74 of the tibial tray 16, respectively. Generally, the system 10 includes various femoral components 12 and tibial trays 16 of different sizes. The surgeon selects the femoral component 12 and tibial tray 16 based on an anatomy of the patient's knee. The femoral component 12 is coupled to the end of the femur by inserting the post 24 into the intramedullary canal of the femur. Likewise, the tibial tray 16 is coupled to the tibia by inserting the stem 74 into the intramedullary canal of the tibia.

The surgeon then selects a tibial insert 18 from a plurality of tibial inserts 18 having different sizes. Each tibial insert 18 may have different sized and shaped condyle surfaces 30, 32. The surgeon tests a range of motion of the system 10 by moving the femoral component 12 through a first range of motion between a fully extended position and a fully flexed position. During flexion of the system 10, the surgeon evaluates the movement of the femoral component 12 along the tibial insert 18. The surgeon may elect to test multiple tibial inserts 18 until a desired range of motion is achieved.

As described below, the tibial insert 18 may also be selected based on a size of the proximal cavity 154 of the tibial insert 18. The size of the proximal cavity 154 varies to provide rotation between the modular insert 22 and the tibial insert 18.

A posterior component 170 is selected to couple to the tibial insert 18 from a plurality of posterior components 170. Each of the posterior components 170 includes a tab 134 having different sized planar side walls 140 and curved side walls 142. In some embodiments, the posterior component 170 is formed integrally with the tibial insert 18, and each tibial insert 18 has a different sized tab 134. With the posterior component 170 coupled to the tibial insert 18, the surgeon test a range of rotation of the tibial insert 18 relative to the tibial tray 16. The surgeon selects the posterior component 170 based on a desired range of rotation. In some embodiments, the surgeon may elect to select a posterior component 170 that prevents rotation of the tibial insert 18 relative to the tibial tray 16.

A modular insert 22 is selected from a plurality of modular inserts 22 having different sizes. The size of the modular insert 22 is selected so that the distal section 280 of the modular insert 22 sits in the proximal cavity 154 in a seated position when the system is fully extended. The surgeon again tests the system 10 by flexing the femoral component 12 through the first range of motion. At an intermediate flexion, the femoral component 12 enters a second range of flexion that is within the first range of flexion. The second range of flexion is between the intermediate flexion and the full extension. At the intermediate flexion, the distal section 280 of the modular insert 22 becomes unseated within the proximal cavity 154.

Through the second range of flexion, the distal section 280 is pulled upward within the proximal cavity 154 so that the modular insert 22 is allowed to rotate relative to the tibial insert 18. The surgeon tests the range of rotation of the modular insert 22 and selects a modular insert 22 that provides a desired range of flexion. In some embodiments, the surgeon may elect to use a different tibial insert 18 with a different sized proximal cavity 154 to achieve the desired range of rotation. The surgeon may also select the modular insert 22 and tibial insert 18 based on a range of motion the second range of flexion.

Accordingly, during the procedure the surgeon tests multiple ranges of motion to select the desired components. The surgeon evaluates the first range of motion from full extension to full flexion, as well as, the second range of motion from the intermediate flexion to full flexion. Further, the surgeon evaluates a first range of rotation of the tibial insert 18 relative to the tibial tray 16, and a second range of rotation of the modular insert 22 relative to the tibial insert 18. It should be noted that the second range of rotation may be within the first range of rotation.

Figures 12, 13:
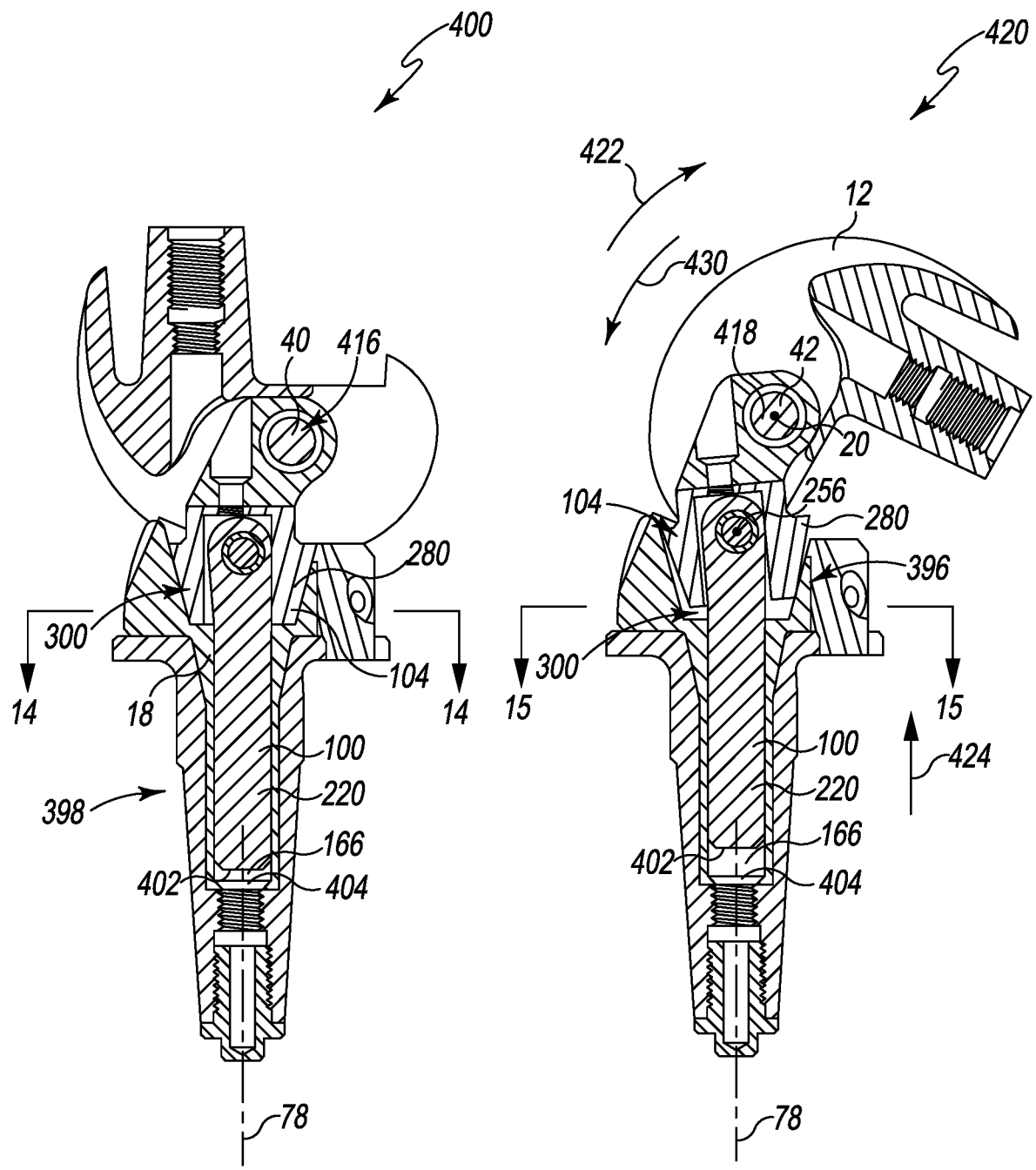
FIG. 12 is a cross-sectional view of the orthopaedic knee prosthesis system in an extended position taken along line 12-12 shown in FIG. 11.
FIG. 13 is a view similar to FIG. 12 showing the orthopaedic knee prosthesis system in a flexed position.
Figure 14:
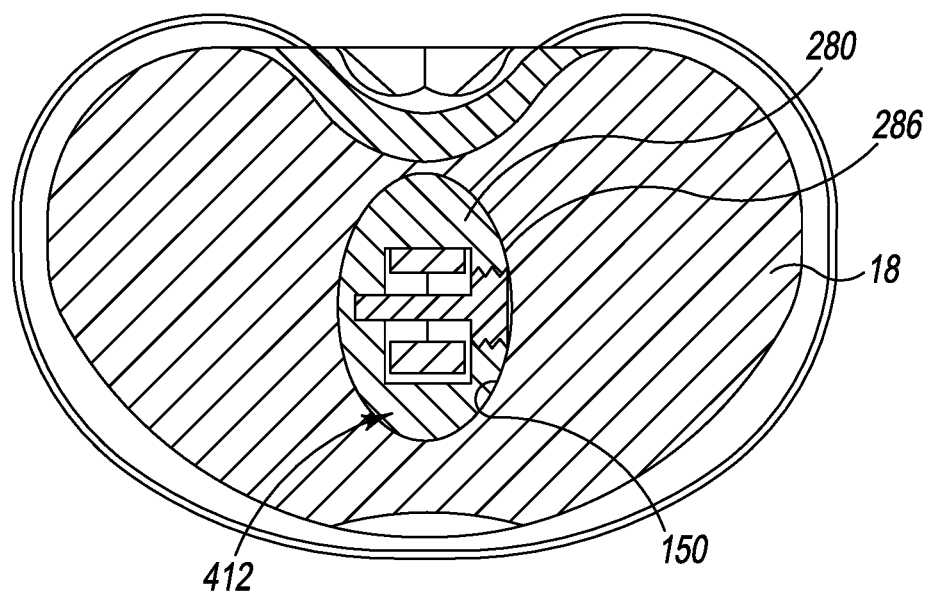
FIG. 14 is a cross-sectional view of the orthopaedic knee prosthesis system in an extended position taken along line 14-14 shown in FIG. 12.

Referring now to FIG. 12, in a fully extended position 400, the elongated stem 100 extends into the distal cavity 166 of the tibial insert 18 to an inferior position 398 such that a tip 402 of the distal end 220 is positioned adjacent a bottom 404 of the distal cavity 166. The elongated stem 100 extends along the longitudinal axis 78. The distal section 280 of the proximal body 104 of the modular insert 22 is seated in the cavity 300. The hinge pin 42 is located in a fully extended position 416. As illustrated in FIG. 14, the outer side wall 286 of the distal section 280 is positioned against the inner wall 150 of the tibial insert 18. The outer side wall 286 of the distal section 280 is in contact with the inner wall 150 of the tibial insert 18 to prevent medial-lateral rotation of the modular insert 22 relative to the tibial insert 18 and to maintain the modular insert 22 in a fixed position 412.

Referring to FIG. 13, in a fully flexed position 420, the femoral component 12 is rotated about the longitudinal axis 20, as indicated by arrow 422, over the first range of flexion, which includes the second range of flexion. In some embodiments, the first range of flexion is within a range of −3 to 140 degrees. Engagement of curved convex condyle surfaces 30, 32 and the curved proximal surfaces 58, 60 during the first range of flexion causes the modular insert 22 to move upward in the proximal cavity 154 from the inferior position 398 to a superior position 396. As the femoral component 12 rotates, the elongated stem 100 moves in a superior direction, as indicated by arrow 424, within the distal cavity 166 to the superior position 396 so that the tip 402 of the distal end 220 advances away from the bottom 404 of the distal cavity 166. The proximal body 104 of the modular insert 22 also advances in the superior direction, so that the distal section 280 is raised in the cavity 300.

The proximal body 104 of the modular insert 22 then rotates about the longitudinal axis 256 relative to the elongated stem 100, as indicated by arrow 430, over the second range of motion from the intermediate flexion to full extension. In some embodiments, the second range of flexion is within 3 to 10 degrees. The second range of motion overlaps the first range of motion. During the second range of flexion of the femoral component 12, the longitudinal axis 20 moves relative to the longitudinal axis 256 over the second range of motion. As the longitudinal axis 20 moves relative to the longitudinal axis 256 the hinge pin 42 moves between the fully flexed position 416 and a fully extended position 418. The second position 418 is located anterior of the first position 416.

Figure 15:
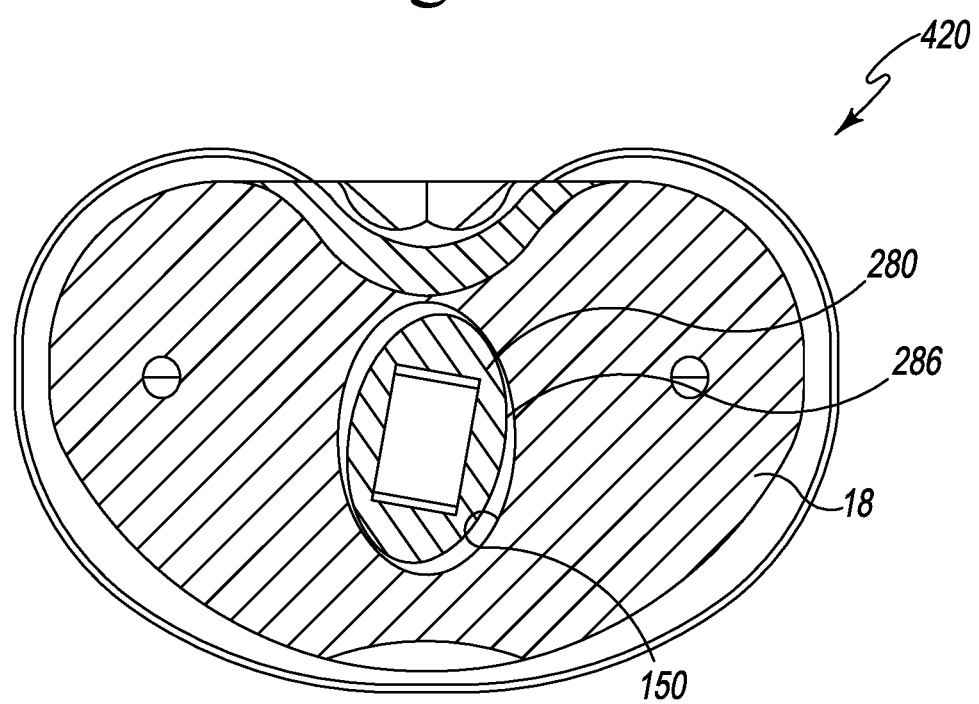
FIG. 15 is a cross-sectional view of the orthopaedic knee prosthesis system in a flexed position taken along line 15-15 shown in FIG. 13.
Figure 16:
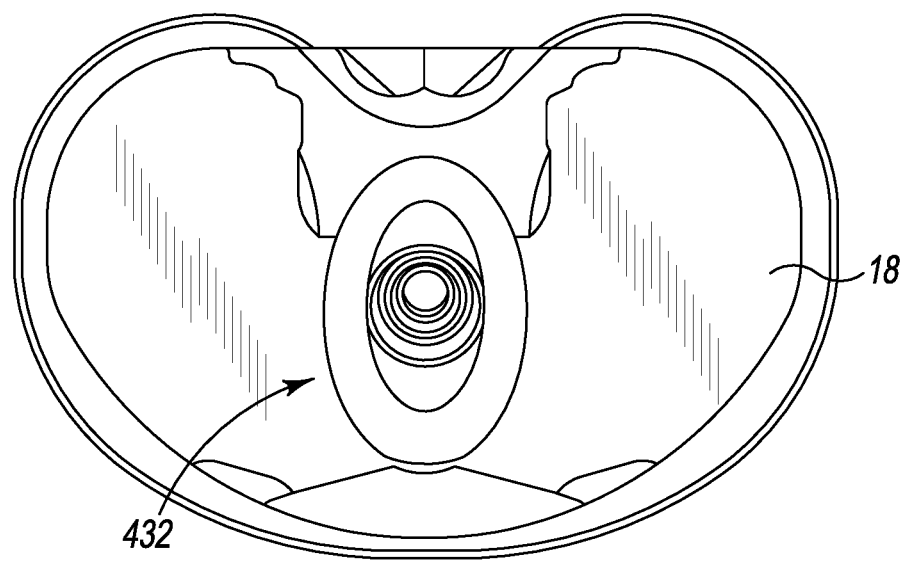
FIG. 16 is a top plan view of the modular insert and tibial insert shown in FIG. 1 with the modular insert in a rotated position.

As illustrated in FIG. 15, during the second range of flexion, the outer side wall 286 of the distal section 280 is separated from the inner wall 150 of the tibial insert 18, thereby enabling medial-lateral rotation of the modular insert 22 relative to the tibial insert 18. The modular insert 22 rotates about the longitudinal axis 78 to a rotated position 432, an example of which is provided in FIG. 16.

When the femoral component 12 is returned to the extended position 400, the modular insert 22 advances distally into the distal cavity 166 so that the outer side wall 286 of the distal section 280 engages the inner wall 150 of the tibial insert 18, thereby rotating the modular insert 22 back to the fixed position 412.

Figure 17:
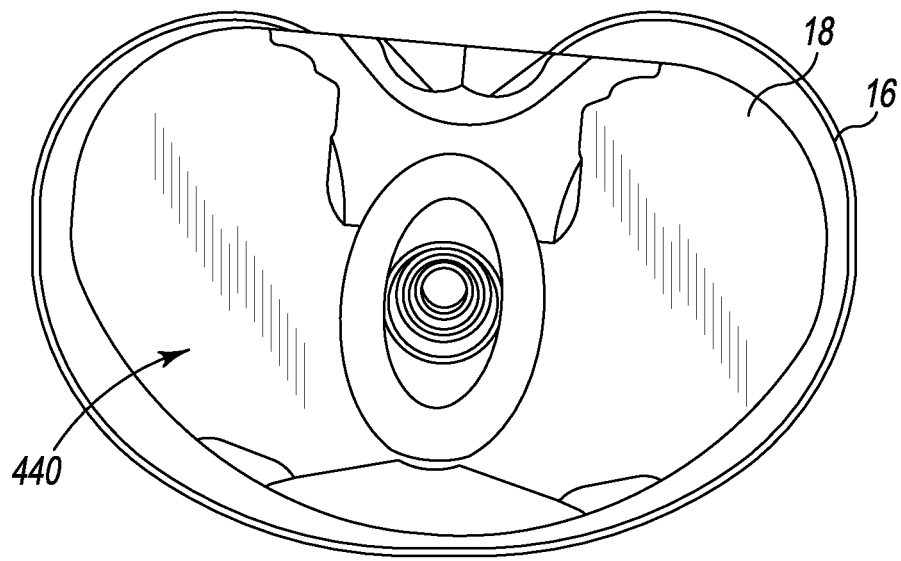
FIG. 17 is a top plan view of the tibial insert and the tibial tray shown in FIG. 1 with the tibial insert in a rotated position.

Referring now to FIG. 17, the tibial insert 18 is also capable of rotating medially-laterally relative to the tibial tray 16 in some embodiments. In embodiments where the curved side wall 142 of the tab 134 is sized smaller than the curved side wall 206 of the channel 66, the tibial insert 18 rotates about the longitudinal axis 78 in either the extended position 400 or the flexed position 420. The tibial insert 18 is permitted to rotate either medially or laterally to a rotated position 440, an example of which is provided in FIG. 17. A range of rotation is determined by a size of the tab 134. A smaller tab 134 will provide more rotation than a larger tab 134. The tibial insert 18 is permitted to rotate until the curved side wall 142 of the tab 134 contacts the curved side wall 206 of the channel 66.

While the disclosure has been illustrated and described in detail in the drawings and foregoing description, such an illustration and description is to be considered as exemplary and not restrictive in character, it being understood that only illustrative embodiments have been shown and described and that all changes and modifications that come within the spirit of the disclosure are desired to be protected.

There are a plurality of advantages of the present disclosure arising from the various features of the devices and assemblies described herein. It will be noted that alternative embodiments of the devices and assemblies of the present disclosure may not include all of the features described yet still benefit from at least some of the advantages of such features. Those of ordinary skill in the art may readily devise their own implementations of the devices and assemblies that incorporate one or more of the features of the present invention and fall within the spirit and scope of the present disclosure as defined by the appended claims.

The invention claimed is:

1. An orthopaedic prosthesis, comprising:
    a femoral component configured to be attached to a distal end of a patient's femur,
    a tibial tray configured to be attached to a proximal end of a patient's tibia, the tibial tray including (i) a base having an outer surface, (ii) a post extending distally from the base, and (iii) an aperture extending defined in the post and the base,
    a tibial insert configured to rotate relative to the tibial tray, the tibial insert including (i) a platform shaped to engage the base of the tibial tray, (ii) a stem extending distally from the platform and received in the aperture of the tibial tray, (iii) a cavity extending longitudinally through the platform, and (iv) a tab coupled to the platform, the tab being configured to engage the outer surface of the base to limit rotation of the tibial insert relative to the tibial tray, and
    a modular insert is received in the cavity defined in the tibial insert, the modular insert including (i) an elongated stem, and (ii) a body rotatably coupled to the elongated stem,
    wherein the femoral component is rotatably coupled to the body of the modular insert, the femoral component being configured to rotate about a first axis relative to the tibial insert over a first range of motion, the first axis extending in a medial-lateral direction, and
    wherein the body of the modular insert is configured to rotate relative to the tibial insert about a second axis extending parallel to the first axis over a second range of motion, the second range of motion being less than the first range of motion.

2. The orthopaedic prosthesis of claim 1, wherein the body of the modular insert is configured to rotate relative to the femoral component to move the first axis relative to the second axis over the second range of motion.

3. The orthopaedic prosthesis of claim 1, further comprising an elongated pin connecting the femoral component to the body of the modular insert, wherein the elongated pin defines the first axis and is moveable between a first position and a second position relative to the tibial insert over the second range of motion, the second position being located anterior of the first position.

4. The orthopaedic prosthesis of claim 3, wherein:
the modular insert is configured to move in a superior-inferior direction relative to the tibial insert over the second range of motion between an inferior position and a superior position,
when the modular insert is positioned in the inferior position, the elongated pin is in the first position, and
when the modular insert is positioned in the superior position, the elongated pin is in the second position.

5. The orthopaedic prosthesis of claim 4, wherein:
the tibial insert includes an inner wall that defines the cavity, the inner wall including a tapered proximal surface that defines a proximal section of the cavity, and
the body of the modular insert is seated in the proximal cavity section when the modular insert is positioned in the inferior position.

6. The orthopaedic prosthesis of claim 5, wherein the inner wall of the tibial insert includes an inferior base surface, and the tapered proximal surface of the tibial insert extends from an elongated opening defined in the platform to the inferior base surface.

7. The orthopaedic prosthesis of claim 6, wherein the elongated opening has a substantially oval shape.

8. The orthopaedic prosthesis of claim 6, wherein:
an opening is defined in the inferior base surface,
the inner wall of the tibial insert includes a distal surface that defines a distal section of the cavity, and
the elongated stem of the modular insert extends into the distal cavity section.

9. The orthopaedic prosthesis of claim 5, wherein:
the elongated stem of the modular insert defines a longitudinal axis, and
the modular insert is permitted to rotate about the longitudinal axis relative to the tibial insert when the modular insert is positioned in the superior position.

10. The orthopaedic prosthesis of claim 1, wherein the tab is removably coupled to the platform of the tibial insert.

11. The orthopaedic prosthesis of claim 1, wherein the first range of motion is in a range of −3 to 140 degrees of flexion.

12. The orthopaedic prosthesis of claim 11, wherein the second range of motion is in a range of 3 to 10 degrees of flexion.

13. An orthopaedic prosthesis system, comprising:
a first implantable prosthetic component that is configured to be attached to a distal end of a patient's femur, the first implantable prosthetic component including (i) a first body having a pair of spaced apart curved convex condyle surfaces, (ii) a second body rotatably coupled to the first body, and (iii) an elongated stem rotatably coupled to the second body,
a second implantable prosthetic component that is configured to be attached to a proximal end of a patient's tibia, and
an insert prosthetic component configured to be positioned between the first implantable prosthetic component and the second implantable prosthetic component, the insert prosthetic component including a cavity sized to receive the elongated stem of the first implantable prosthetic component,
wherein the first body is configured to rotate about a first axis relative to the insert prosthetic component over a first range of motion, the first axis extending in a medial-lateral direction, and
wherein the second body is configured to rotate relative to the insert prosthetic component about a second axis extending parallel to the first axis over a second range of motion, the second range of motion being less than the first range of motion.

14. The orthopaedic prosthesis system of claim 13, further comprising an elongated pin connecting the first body to the second body, wherein the elongated pin defines the first axis and is moveable between a first position and a second position relative to the insert prosthetic component over the second range of motion, the second position being located anterior of the first position.

15. The orthopaedic prosthesis system of claim 14, wherein:
the second body of the first implantable prosthetic component is configured to move in a superior-inferior direction relative to the insert prosthetic component over the second range of motion between an inferior position and a superior position,
when the second body is positioned in the inferior position, the elongated pin is in the first position, and
when the second body is positioned in the superior position, the elongated pin is in the second position.

16. The orthopaedic prosthesis system of claim 15, wherein:
the insert prosthetic component includes a pair of curved proximal surfaces, and the pair of spaced apart curved convex condyle surfaces of the first body are configured to engage the curved proximal surfaces, and
the curved convex condyle surfaces and the curved proximal surfaces are shaped such that the engagement of curved convex condyle surfaces and the curved proximal surfaces over the second range of motion causes the second body of the first implantable prosthetic component to move between the inferior position and the superior position.

17. The orthopaedic prosthesis system of claim 13, wherein the second range of motion overlaps with the first range of motion.

18. The orthopaedic prosthesis system of claim 13, wherein the first range of motion is in a range of −3 to 140 degrees of flexion.

19. The orthopaedic prosthesis system of claim 13, wherein the second range of motion is in a range of 3 to 10 degrees of flexion.

20. An orthopaedic prosthesis system, comprising:
a first implantable prosthetic component that is configured to be attached to a distal end of a patient's femur and includes a pair of spaced apart curved convex condyle surfaces,
a second implantable prosthetic component that is configured to be attached to a proximal end of a patient's tibia,
an insert prosthetic component positioned between the first implantable prosthetic component and the second implantable prosthetic component, the insert prosthetic component including a pair of curved proximal surfaces engaged with the pair of spaced apart curved convex condyle surfaces, and
an elongated pin extending along a first axis, the elongated pin rotatably coupling the insert prosthetic component to the first implantable prosthetic component,
wherein the first implantable prosthetic component is configured to rotate about the first axis relative to the insert prosthetic component over a range of motion, the first axis extending in a medial-lateral direction, and wherein the curved convex condyle surfaces and the curved proximal surfaces are shaped such that the engagement of curved convex condyle surfaces and the curved proximal surfaces over the range of motion causes the elongated pin to move between a first position and a second position, the second position being located anterior of the first position.

* * * * *